United States Patent [19]

Matich

[11] Patent Number: 5,797,146
[45] Date of Patent: Aug. 25, 1998

[54] BREATH DEFLECTOR WITH SEAL

[76] Inventor: Ronald D. Matich, P.O. Box 2541, Baxter, Minn. 56401

[21] Appl. No.: 752,857

[22] Filed: Nov. 21, 1996

[51] Int. Cl.$^6$ .............................. A42B 3/24; A62B 18/00
[52] U.S. Cl. .............................. 2/424; 2/435; 2/9; 2/173;
351/158; 128/863; 128/206.14; 128/206.25
[58] Field of Search .................................. 2/9, 422, 424,
2/15, 10, 11, 426, 427, 435, 431, 425, 173,
203, 205, 206, 13, 174; 351/158; 128/859,
863, 206.14, 206.24, 206.25

[56] References Cited

U.S. PATENT DOCUMENTS

| | | | |
|---|---|---|---|
| 3,834,384 | 9/1974 | Raines | 128/146.2 |
| 3,888,246 | 6/1975 | Lauer | 128/146.2 |
| 4,538,303 | 9/1985 | Schnitzler | 2/424 |
| 4,547,909 | 10/1985 | Bell | 2/431 |
| 4,556,994 | 12/1985 | Kawasaki et al. | 2/424 |
| 4,641,379 | 2/1987 | Martin | 2/9 |
| 4,653,124 | 3/1987 | McNeal et al. | 2/427 |
| 4,667,348 | 5/1987 | Sundahl | 2/410 |
| 4,686,712 | 8/1987 | Spiva | 2/10 |
| 4,966,140 | 10/1990 | Herzberg | 128/206.19 |
| 5,148,550 | 9/1992 | Hodgkinson et al. | 2/424 |
| 5,704,063 | 1/1998 | Tilden | 2/9 |

FOREIGN PATENT DOCUMENTS

| | | | |
|---|---|---|---|
| 512193 | 11/1992 | European Pat. Off. | 2/422 |
| 6010205 | 1/1994 | Japan | 2/424 |
| 1576647 | 10/1980 | United Kingdom | 2/424 |

*Primary Examiner*—Michael A. Neas

[57] ABSTRACT

A breath deflector sealed across the bridge of the nose and extending forwardly therefrom, such as to the inside portion of a helmet and downwardly beyond the mouth, to prevent the fogging of glasses or the visor of the helmet. The seal of the breath deflector extends from the outside corner of one eye, across the bridge of the nose, and to the outside corner of the other eye to minimize a direct upward flow of moisture from one's breath to the area of vision in front of one's eyes. The breath deflector is resilient to form fit to the bridge of the nose even at temperatures below freezing, moisture-resistant, and insulative. A breath deflector kit includes a set of breath deflecting pieces, a plurality of stand alone skin friendly adhesive strips which are double faced with removable backs for being applied to the breath deflector in the field, and a plurality of swatches made of the same material of the pieces but formed in a different shape for being distinguishable from the breath deflecting pieces for being applied to exposed areas of the face with the adhesive strips. The breath deflector may be used with glasses, goggles, and/or helmets.

20 Claims, 3 Drawing Sheets

U.S. Patent  Aug. 25, 1998  Sheet 1 of 3  5,797,146

BREATH DEFLECTOR WITH SEAL

BACKGROUND OF THE INVENTION

The present invention relates generally to a breath deflector disposed between the mouth and the eyes, particularly to such breath deflectors sealed to the face and extending therefrom, and specifically to such breath deflectors used in helmets by one wearing glasses.

Snowmobiling becomes a dangerous activity when the area in front of the driver's eyes fogs over. The fog, generally caused by the driver's breath, may cover either or both of the inner and outer faces of the lens of the driver's glasses. Further, the fog may cling to the inside face of the visor or other transparent portion of the helmet.

A driver may attempt to control the fogging by wearing a vented helmet to bring outside air in, wearing a helmet with a separator extending from a front portion of the helmet to the nose where the separator form-fits to the nose via resilient wire embedded in the separator, wearing a face mask having a downwardly extending funnel to channel exhaled air downwardly out of the helmet, or fixing layers of duct tape to their faces in a cantilevered fashion so as to extend the duct tape from the face to the helmet.

With the exception of duct tape, these efforts to control the fogging fail to recognize the source of the problem. The present invention addresses the source of the problem, i.e., that the fogging of the glasses occurs because of moisture which travels upwardly along the driver's face, which is almost always covered by a mask. The moisture moves upwardly in the space between the inside of the mask and the skin of the face. Moisture which finds its way to the driver's face may have many sources besides the mouth. For example, sweat from the scalp, face or neck generated by the high tech insulated helmets and snow stuck in the helmet or blowing in through the vents are two sources of moisture which may find their way to the driver's face where such may evaporate under the heat of the face and travel upwardly to fog the glasses.

The duct tape solution fails to address other problems. For example, duct tape is not moisture resistant. Nor is duct tape insulative. Nor is duct tape resilient. Further, one entire side or face of duct tape is sticky and only a portion of this sticky surface is actually affixed to the face. The other portion of the sticky surface is exposed and extends out to collect dirt or dust in an area directly above the mouth and nose.

SUMMARY OF THE INVENTION

A general object of the present invention is to provide a unique breath deflector.

Another object of the invention is to provide a unique seal for such breath deflector. The seal is placed between the eyes and the mouth and over the bridge of the nose to minimize an upward conveyance of moisture or air from the mouth and nose to the eyes.

Another object of the invention is to provide a unique width to the breath deflector. The breath deflector is of a width sufficient (or the seal is of a length sufficient) to extend between the outer corner edge portions of the eyes so as to divert moisture around the eyes and glasses. The width of the breath deflector is further sufficient to extend beyond the corners of the mouth.

Another object of the invention is to provide a unique length to the breath deflector. Such a length preferably extends beyond the nose and more preferably extends beyond the mouth. In a helmet, the length of the breath deflector is sufficient to extend to an inside portion of the helmet, as well as to a position over the nose and mouth.

Another object of the invention is to provide a unique material for such a breath deflector. The breath deflector is preferably formed from a material which is resilient to form-fit to the bridge of the nose even at temperatures below freezing, which is moisture resistant, and which is insulative. More preferably, such material has cells with trapped air therein. Even more preferably, such material is a closed cell foam with the cells having trapped air therein. Most preferably, such material is a closed cell foam polyethylene having bubbles of air or gas trapped therein.

Another object of the invention is to provide a unique breath deflector kit. The kit includes a set of pieces of such material for use as breath deflectors and a plurality of skin friendly adhesive strips which are double faced with removable backings, which carry out the role of the seal and fix the breath deflector to the face of the driver. The kit may optionally include swatches of such material for application to exposed areas of the face, such as when the driver forgoes the helmet visor for goggles. The swatches may be applied with the adhesive strips.

The advantages of the invention are numerous. Snowmobiling safety is enhanced. The breath deflector is soft and thus comfortable, disposable, easy to use, sanitary, reusable, and inexpensive. It is insulative; it helps protect the nose and cheeks from frostbite. It fits under any helmet with ease. There are no straps, hooks or Velcro® to manipulate. The breath deflector stays securely in place.

These and further objects and advantages of the present invention will become clearer in light of the following detailed description of the illustrative embodiments of this invention described in connection with the drawings.

BRIEF DESCRIPTION OF THE DRAWINGS

The illustrative embodiments may be best described by reference to the accompanying drawings where.

Figure 1:
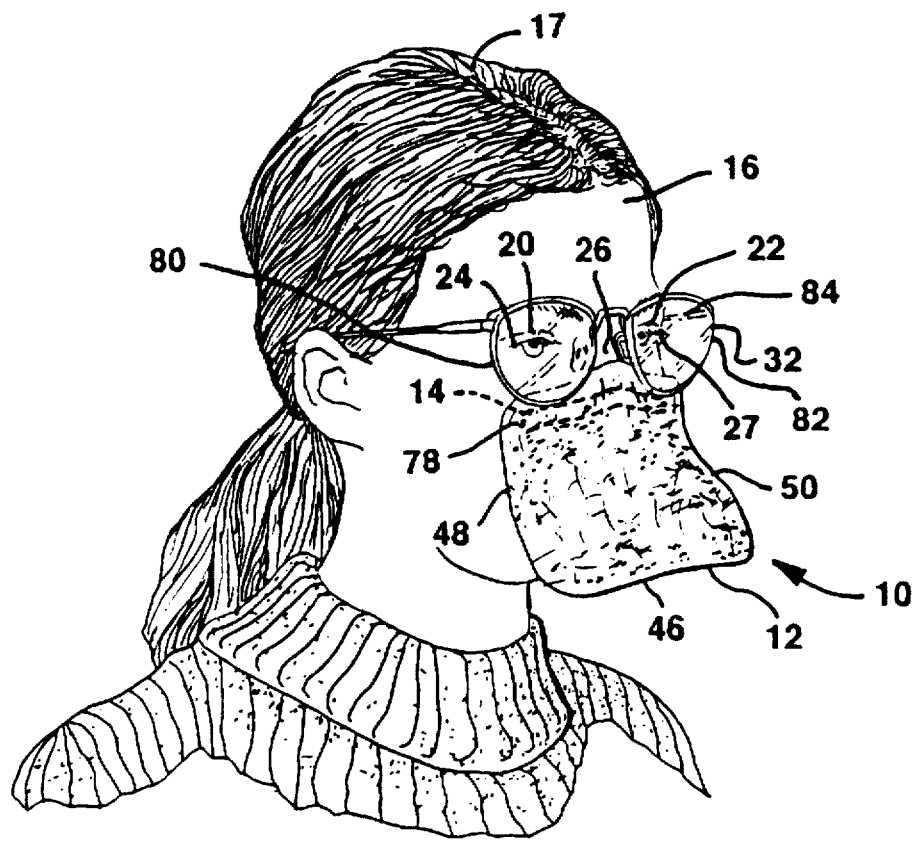
FIG. 1 is a perspective view of the breath deflector in use with glasses.

All Figures are drawn for ease of explanation of the basic teachings of the present invention only; the extensions of the Figures with respect to number, position, relationship, and dimensions of the parts to form the preferred embodiment will be explained or will be within the skill of the art after the following description has been read and understood. Further, the exact dimensions and dimensional proportions to conform to specific force, weight, strength, and similar requirements will likewise be within the skill of the art after the following description has been read and understood.

Where used in the various figures of the drawings, the same numerals designate the same or similar parts.

Furthermore, when the terms "side", "inner", and "outer", and similar terms are used herein, it should be understood that these terms have reference only to the structure shown in the drawings as it would appear to a person viewing the drawings and are utilized only to facilitate describing the preferred embodiments.

DESCRIPTION

Figure 2:
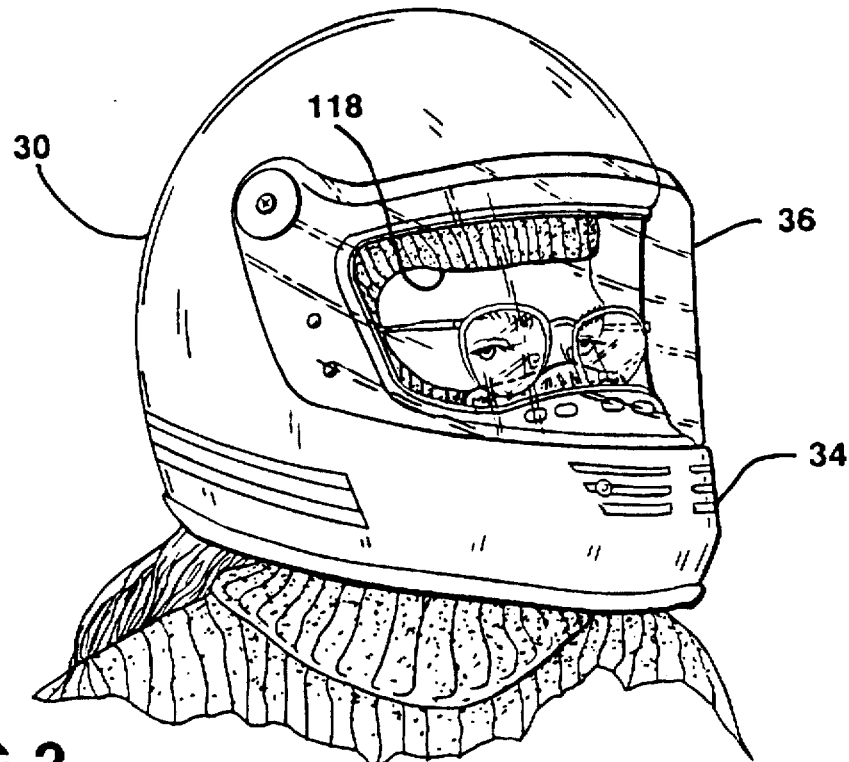
FIG. 2 is a perspective view of the breath deflector in use with a snow mask and snowmobile helmet.
Figure 3:
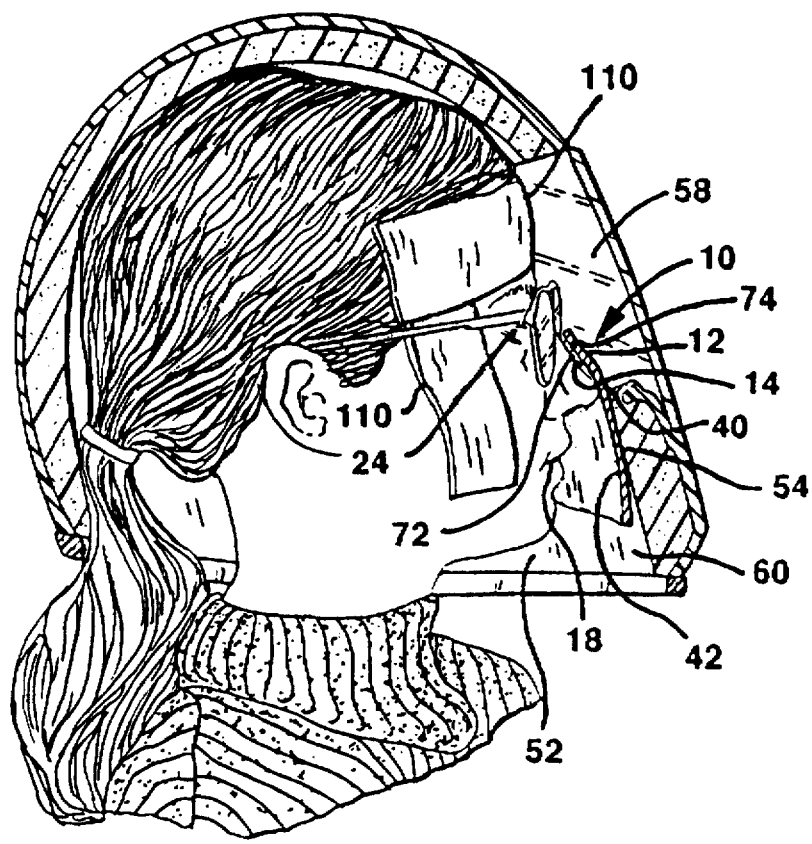
FIG. 3 is a section view of the breath deflector in use with a snowmobile helmet.

As shown in FIG. 1, the present breath deflector is designated in general by the reference numeral 10. The breath deflector 10 generally includes an insulative flexible piece 12 and a flexible seal 14. The seal 14 is affixed to the face 16 of a person 17 between the mouth 18 and the eyes 20, 22. The seal 14 of the breath deflector 10 preferably extends from a position beyond or immediately downwardly of one outside corner edge eye portion 24 (lateral palpebral commissure), across the nose bridge 26, to a position beyond or immediately downwardly of the other corner edge eye portion 27 (lateral palpebral commissure). As shown in FIG. 2, the breath deflector 10 may be used with an insulative sock mask 28 (hat or cap) and a helmet 30 or, as shown in FIG. 3, the breath deflector 10 may be used with just a helmet 30. The user 17 may wear glasses 32. The helmet 30 may include vents 34 and a swingable visor 36.

Figure 4:
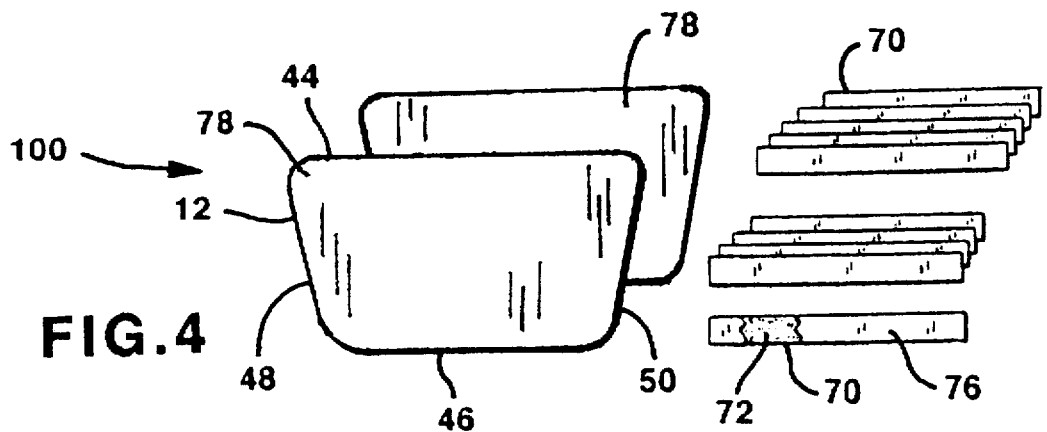
FIG. 4 is an elevation view of a breath deflector kit having breath deflector pieces and adhesive strips.

As shown in FIGS. 3 and 4, the insulative piece 12 includes a pair of opposing faces 40, 42. The insulative piece further includes a pair of respective proximal and distal parallel edges 44, 46 and a pair of oblique or tapered side edges 48, 50 so as to form a trapezoidal shape. Parallel edge 44 is greater in length than parallel edge 46. Side edges 48, 50 taper from edge 44 toward each other to terminate at edge 46. Such tapering accounts for the nose bridge 26 and permits a general even spacing of side edges 48, 50 from side inside portions 52 of the helmet 30. Such a spacing permits air flow between the side edges 48, 50 of the piece 12.

The piece 12 is preferably formed of an insulative material, more preferably of an insulative material with closed cells so as to trap air therein, and even more preferably of an insulative material of a closed cell foam so as to trap air therein. The matrix of cells with an air or gas trapped therein is shown by the shading in FIGS. 4 and 5. Most preferably such insulative material is formed of a closed cell foam polyethylene. The insulation provided by the piece 12 minimizes frost bite on the user's face, such as on the nose and cheeks.

The piece 12 is preferably formed of a material which is resilient. Such resiliency permits the piece 12 to be form-fit to the nose in a sealing fashion. Further, it is preferred that such material maintains its resiliency at temperatures below freezing, and at temperatures well below freezing, such as at 40 degrees below Fahrenheit. Still further such resiliency permits a portion 54 of the piece 12 to bend downwardly to confront the inside portion 52 of the helmet 30, as shown in FIG. 3. Such a resiliently bent portion 54 is formed when the helmet 30 is put on, and divides the area between the helmet 30 and the face 16 into a vision portion 58 and a breathing portion 60. The bottom or distal edge 46 preferably extends beyond the nose and more preferably beyond the mouth 18. However, it is preferred that the distal edge 46 terminates short of the vents 34 of the helmet 30 to permit a free flow of air into the helmet 30 from the vents 34.

The piece 12 is preferably formed of a material which is moisture resistant and which does not absorb moisture. When snowmobiling, a great amount of moisture collects in the helmet 30. This moisture may come from one's breath, snow, sweat, and phlegm. A moisture resistant piece 12 maintains its insulative and resiliency qualities.

The piece 12 is preferably formed of a material which minimizes the permeation of air and water vapor therethrough and is more preferably formed of a material which is substantially impermeable to air and water vapor. Preferably, the material includes closed cells. However, if desired, an open cell material may be used. Among the various types of open cell material, that which is substantially moisture resistant and substantially nonabsorbent is preferred.

As shown in FIGS. 3 and 4, the seal 14 includes an elongate flexible base strip 70 having opposite faces 72, 74. On each of the faces 72, 74 is a skin friendly adhesive. The adhesive is preferably biocompatible with the skin of the nose. The adhesive is preferably a pressure sensitive adhesive. The flexible strip 70 may be an acrylic pressure sensitive strip. If desired, the adhesive may be rubber-based. The strip 70 may be obtained from Davlyn Inc. of St. Paul, Minn. under number 501. Prior to being applied to the insulative piece 12, each of the faces 72, 74 is covered by an elongate, flexible, substantially air tight, removable backing 76. It should be noted that the seal 14, including the strip 70 and its adhesive, is preferably moisture resistant and preferably does not absorb moisture. Strip 70 may be cloth or fabric, plastic or formed from a polymer or copolymer. If cloth or fabric, the strip 70 is sufficiently impregnated with the adhesive such that the strip 70 is moisture resistant and, more preferably, does not absorb moisture. Backing 76 may be paper or plastic.

The strip or seal 70 is applied to a proximal end portion 78 of the piece 12. The length of the strip 70 is sufficient to extend between the outer corner edge eye portions 24 and 27 or between the outer edge portions 80, 82 of the lens 84 of glasses 32 which may be worn by the user 17 of the breath deflector 10. The width of the strip or seal 70 is sufficient to provide a sufficient amount of adhesive to adhere to the skin of the face to prevent accidental removal, such as when the helmet 30 is removed from the head.

A breath deflector kit 100 includes a pair of breath deflector pieces 12, and a plurality, such as ten, adhesive strips 70. The thickness of the pieces 12 is preferably one-eighth inches to one-thirty-seconds of an inch. The length of the upper edge 44 (between the curved or converging corners) is about 5 and one-half inches. The length of the lower edge 46 (between the curved or converging corners) is about four inches. The length of the piece 12, between the upper and lower edges 44 and 46 is about three and five-eighth inches. The piece 12 can be placed in at different heights on the bridge of the nose. For example, smaller adults may place the piece 12 at a higher place on the bridge of the nose.

Preferably, the color of the pieces 12 is dark, such as black, so as to absorb the heat of the sun and further minimize the chances of frostbite. Further, the dark color is nonreflective so as to minimize the chances of glare or light temporarily blinding the driver.

Figure 5:
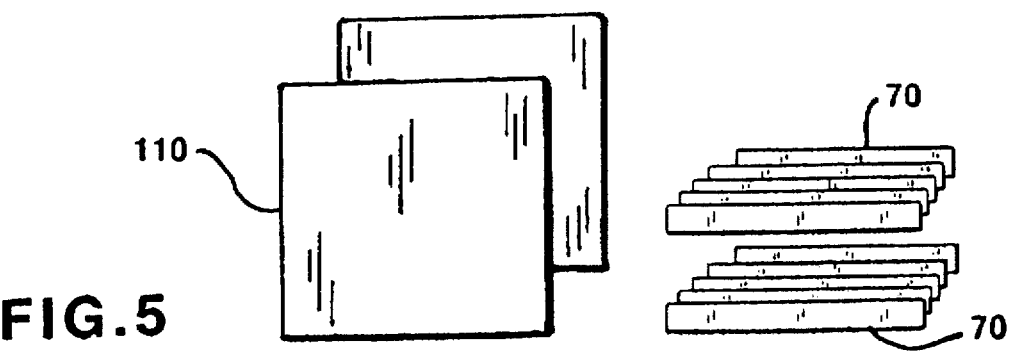
FIG. 5 is an elevation view of insulative swatches for exposed portions of the skin and adhesive strips for applying the insulative swatches in combination with the kit of FIG. 4.
Figure 6:
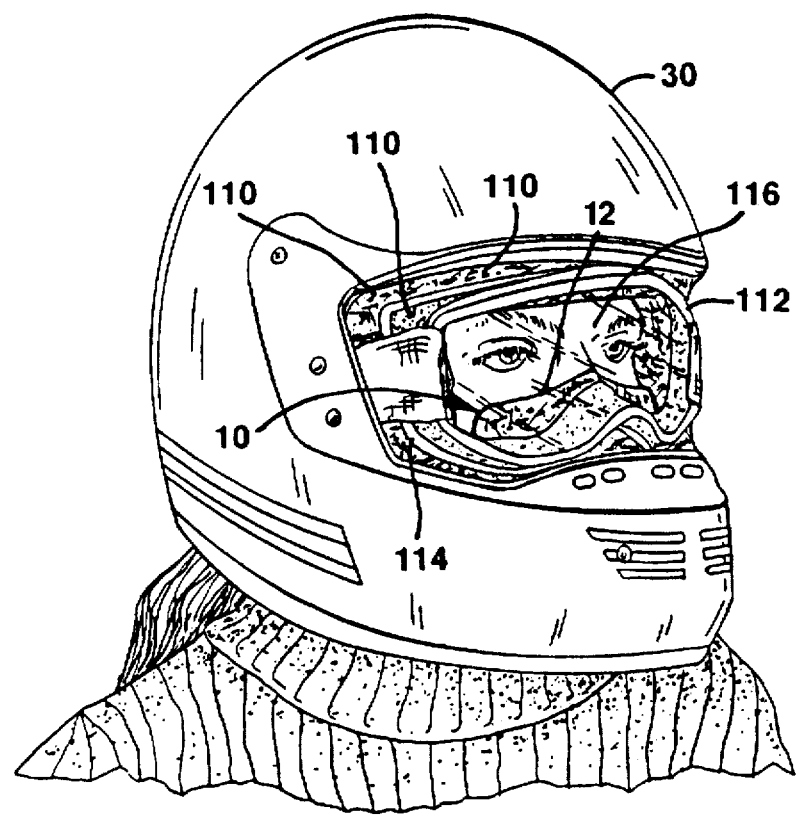
FIG. 6 is a view of the breath deflector in use with goggles and a visorless snowmobile helmet, and with the insulative swatches of FIG. 5.

As shown in FIG. 5, the breath deflector kit 100 may further include a set of swatches 110 formed of the insulative material from which piece 12 is formed and may further include additional adhesive strips 70. Swatches 110 are preferably of a different shape (such as a square shape) than the pieces 12 so that the swatches 110 may be distinguished from the pieces 12. Swatches 110 are included for attachment to exposed skin, such as shown in FIGS. 3 and 6. For example, a snowmobiler may remove the visor 36 of the helmet 30 and wear goggles 112. The goggles 112 may have a resilient portion or seal 114 about the lens 116. The goggles 112 may be conventional ski goggles. Even wearing a mask, such as a sock mask 118, the snowmobiler wearing the goggles 112 may have exposed skin. In such a case, swatches 110 may be applied to the exposed skin with the adhesive strips 70. The adhesive strips 70 may be applied about the periphery of the swatch 110 to be affixed to the skin, or may cover one entire face of the swatch 110.

In operation, the face may first be cleaned to remove oil from the skin. Then, a mask, such as the sock mask 118 is optionally pulled over the head. Then, one of the faces 76 is peeled off the adhesive strip or seal 70 and the exposed adhesive 74 of the seal 70 is applied to the proximal end portion 78 of the piece 12. Pressure, such as with a finger, is then applied to the backing 76 which remains on the seal 70 or to the opposite face of the piece 12 to affix the seal 70 to the piece 12. Then the backing 76 which remains on the seal 70 is peeled off and the piece 12 is centered on the nose bridge 26. Then pressure, such as with a finger, is applied to the outside face of the piece 12 along the seal 70 to affix the breath deflector 10 to the face 16. Then the helmet 30 is pulled over the head and subsequently, if the driver wears glasses, the glasses 32 are put on through the open area of the helmet 30 which the visor 36 covers. The visor 36 is swung down and the driver is ready for fog-free snowmobiling. The process is reversed for removal of the breath deflector 10.

During snowmobiling or some other activity where helmets are used, such as motorcross or autoracing, the seal 70 and piece 12 are substantially moisture and air tight, and the seal 70 is of a sufficient length to extend between the outer corner edge portions 24 and 27 of the eyes 20 and 22 so as to minimize a fogging of the lens 84 of the glasses 32 or a fogging of other vision means such as the goggles 112 or a visor 36 of the helmet 30.

After such activity, the breath deflector 10 may be easily removed, stuck on the top of the helmet 30 during a break in the activity, removed from the helmet 30, and reapplied to the face 16. If the seal 70 breaks down, another seal 70 may be reapplied over the existing seal 70. After use, the breath deflector 70 may be disposed of, and hence the breath deflector 10 is sanitary.

Figure 7:
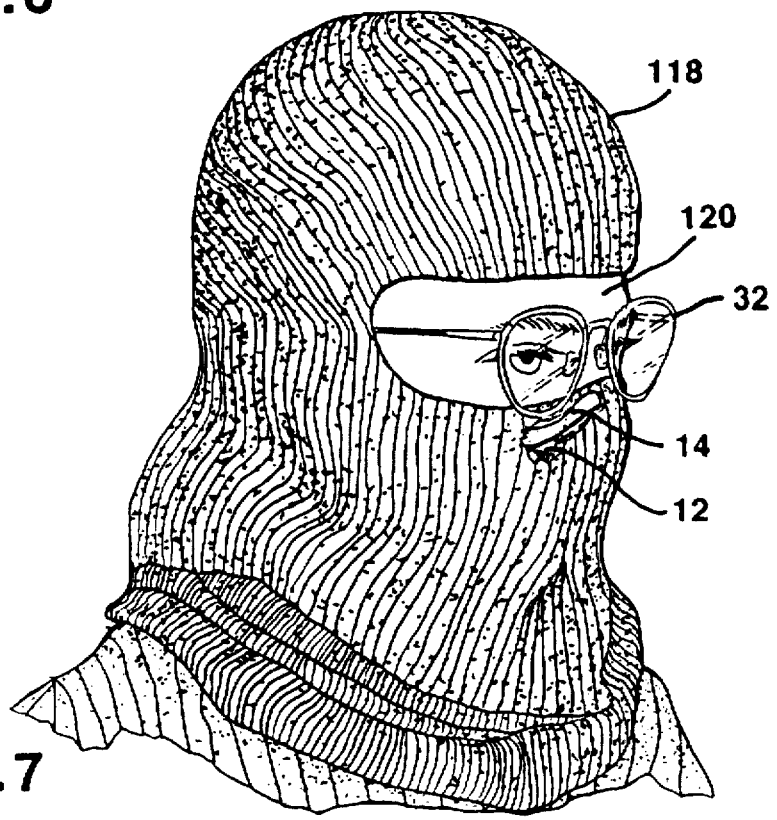
FIG. 7 is a partially broken away view of the breath deflector in use under a sock mask.

In another use of the invention, as shown in FIG. 7, the breath deflector 10 may be worn under a sock mask 118. Sock mask 118 is preferably formed of a breathable, insulative, flexible material such as wool. The length of the mask 118 is sufficient to cover the head and neck and come to rest on the shoulders. The sock mask 118 is tube like. The sock mask 118 includes an opening 120 for the eyes only. It should be noted that, if desired, the breath deflector piece 12 may be sewn or otherwise affixed to the inner side of the mask 118.

Thus since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes which come within the meaning and range of equivalents of the claims are intended to be embraced therein.

I claim:

1. A breath deflector in combination with a helmet and sealed across the bridge of a nose and extending generally forwardly from the nose to an inside portion of the helmet, comprising:

a) a piece having first and second opposite faces defining a thickness, proximal and distal end edge portions defining a length, and side edge portions defining a width;

b) with the piece being formed of a polymeric material which is insulative;

c) with the material further being substantially impermeable to air and water vapor;

d) with the width of the piece along the proximal end edge portion being at least approximately the distance between the outer corner portions of the eyes of an average sized adult such that breath is deflected away from the eyes;

e) with the length of the piece being at least approximately the distance from the bridge of the nose to the inside portion of the helmet in a general forwardly direction whereby breath is deflected away from a transparent portion of the helmet; and f) a skin-friendly seal on at least a section of the proximal end edge portion such that the proximal end edge portion is sealable across the bridge of the nose, with the length of the seal being at least approximately the distance between the outer corner portions of the eyes of an average sized adult such that the permeation of moisture and air is minimized between the proximal end edge portion and the bridge of the nose and other portions of the face to which the seal is affixed whereby fogging of glasses or the transparent portion of the helmet is minimized.

2. The breath deflector of claim 1 wherein the length of the piece is at least sufficient to extend downwardly beyond the mouth.

3. The breath deflector of claim 1 wherein the width of the piece along the distal end edge portion is at least sufficient to extend beyond the corners of the mouth.

4. The breath deflector of claim 1 wherein the material comprises closed cells having air trapped therein, with the closed cells being distributed over said length of said piece and over said width of said piece.

5. The breath deflector of claim 1 wherein the material is resilient such that proximal end edge portion form fits to the bridge of the nose and such that the distal end edge portion is resiliently bendable against the inside portion of the helmet whereby the distal end edge portion bends downwardly when the helmet is pulled over one's head.

6. The breath deflector of claim 1 wherein the material is resilient at temperatures less than about zero degrees C.

7. The breath deflector of claim 1 wherein the width of the piece extends short of side portions of the helmet to permit air flow along side portions of the face and helmet.

8. The breath deflector of claim 1 wherein the piece is relatively thin so as to have generally a thickness of a swatch, wherein the piece includes an upper edge portion, a lower edge portion, and opposing side edge portions between the upper and lower edge portions, wherein the skin-friendly seal is on at least a section of the upper edge portion, and wherein the lower edge portion and opposing side edge portions remain generally unrestricted of either a user's face or helmet when the skin-friendly seal is engaged with the face.

9. In combination with a helmet, a breath deflector sealed across the bridge of a nose and extending generally forwardly beyond the nose, comprising:

a) a piece having first and second opposite faces defining a thickness, proximal and distal end edge portions defining a length, and side edge portions defining a width;

b) with the piece being formed of a polymeric material which is insulative;

c) with the material further being substantially impermeable to air and water vapor;

d) with the width of the piece being at least approximately the distance between the outer corner portions of the eyes of an average sized adult such that breath is deflected away from the eyes;

e) with the length of the piece being at least approximately the distance from the bridge of the nose to a point beyond the nose in a general forwardly direction whereby breath is deflected away from an area in front of the eyes; and f) a skin-friendly seal on at least a section of the proximal end edge portion such that the proximal end edge portion is sealable across the bridge of the nose, with the length of the seal being approximately the distance between the outer corner portions of the eyes of an average sized adult such that the permeation of moisture and air is minimized between the proximal end edge portion and the bridge of the nose and other portions of the face to which the seal is affixed whereby fogging of a portion of the helmet in front of the eyes is minimized.

10. The breath deflector of claim 9 wherein the length of the piece is sufficient to extend beyond the mouth, and wherein the width of the piece is sufficient to extend beyond the corner portions of the mouth.

11. The breath deflector of claim 9 wherein the material comprises closed cells having air trapped therein, with the closed cells being distributed over said length of said piece and over said width of said piece.

12. The breath deflector of claim 9 wherein the material is resilient such that proximal end edge portion form fits to the bridge of the nose.

13. The breath deflector of claim 12 wherein the material is resilient at temperatures less than about zero degrees C.

14. The breath deflector of claim 9, with the helmet having an inside front portion, and with the length of the piece being sufficient to extend to the inside front portion of the helmet, with the skin friendly seal solely anchoring the piece to a user's face and with the piece being unengaged relative to the helmet.

15. The breath deflector of claim 9 in combination with a pair of glasses, with the glasses comprising a frame and a pair of transparent portions engaged with the frame, and with the piece being disposed between a portion of the glasses and the skin of the face such that the piece insulates the skin of the face from the glasses.

16. The breath deflector of claim 9 in combination with a pair of goggles, with the goggles comprising a frame, a pair of transparent portions engaged with the frame, and a resilient periphery about each of the transparent portions to minimize air flow to an inside face of the transparent portions, with the resilient peripheries riding on the proximal end edge portion of the piece; and further comprising a swatch portion of said material, with the swatch portion having a surface with said skin friendly seal on at least a section of said surface, and with the swatch portion being affixed with the seal on an exposed portion of the face of the one wearing the goggles.

17. A breath deflector sealed across the bridge of a nose and extending generally forwardly beyond the nose, comprising:

a) a piece having first and second opposite faces defining a thickness, proximal and distal end edge portions defining a length, and side edge portions defining a width;

b) with the piece being formed of a material which is insulative;

c) with the material further being moisture-resistant;

d) with the width of the piece being at least approximately the distance between the outer corner portions of the eyes of an average sized adult such that breath is deflected away from the eyes;

e) with the length of the piece being at least approximately the distance from the bridge of the nose to a point beyond the nose in a general forwardly direction whereby breath is deflected away from an area in front of the eyes;

f) a skin-friendly seal on at least a section of the proximal end edge portion such that the proximal end edge portion is sealable across the bridge of the nose, with the length of the seal being approximately the distance between the outer corner portions of the eyes of an average sized adult such that the permeation of moisture and air is minimized between the proximal end edge portion and the bridge of the nose and other portions of the face to which the seal is affixed whereby fogging of a vision tool in front of the eyes is minimized; and g) a stand alone strip of skin friendly sealing adhesive which comprises a strip portion with two faces, with each of the faces having the skin friendly adhesive thereon, and with each of the faces having a removable backing thereon covering the skin friendly adhesive, with the length of each of the faces being approximately the distance between the outer corner portions of the eyes of an average sized adult whereby the stand alone strip may be applied to the proximal edge end portion over an existing seal or adhesive such as when the existing seal or adhesive deteriorates.

18. A breath deflector kit, comprising, in combination:

a) a set of pieces, i) with each of the pieces having first and second opposite faces defining a thickness, proximal and distal end edge portions defining a length, and side edge portions defining a width;

ii) with each of the pieces being formed of a material which is insulative;

iii) with the material further being moisture-resistant;

iv) with the width of each of the pieces being at least approximately the distance between the outer corner portions of the eyes of an average sized adult such that breath is deflected away from the eyes; and v) with the length of each of the pieces being at least approximately the distance from the bridge of the nose to a point beyond the mouth in a general forwardly and downwardly direction whereby breath is deflected away from an area in front of the eyes; and b) a plurality of skin friendly sealing adhesive strips, i) with each of the strips having two faces, with at least a portion of each of the faces having an adhesive thereon such that one face is affixable to a person's face and such that the other face is affixable to the piece;

ii) with each of the faces having a removable backing thereon covering its respective adhesive; and iii) with the length of each of the faces having the adhesive being at least approximately the distance between the outer corner portions of the eyes of an average sized adult whereby each of the strips may be applied to the proximal edge end portion of one of the pieces or over existing adhesive such as when the existing adhesive deteriorates.

19. The breath deflector kit of claim 18 and further comprising:

a set of swatches of said material, with each of the swatches having a shape different from each of the pieces whereby the swatches may be distinguished from the pieces and whereby the swatches may be affixed to a person's face with the skin friendly adhesive strips.

20. A breath deflector kit, comprising, in combination:

a) a piece,
   i) with the piece having first and second opposite faces defining a thickness, proximal and distal end edge portions defining a length, and side edge portions defining a width;
   ii) with the piece being formed of a material which is insulative;
   iii) with the material further being moisture-resistant;
   iv) with the width of the piece being at least approximately the distance between the outer corner portions of the eyes of an average sized adult such that breath is deflected away from the eyes; and
   v) with the length of the piece being at least approximately the distance from the bridge of the nose to a point beyond the mouth in a general forwardly and downwardly direction whereby breath is deflected away from an area in front of the eyes; and b) a set of skin friendly sealing adhesive strips,
   i) with each of the strips having two faces, with at least a portion of each of the faces having an adhesive thereon such that one face is affixable to a person's face and such that the other face is affixable to the piece;
   ii) with each of the faces having a removable backing thereon covering its respective adhesive; and
   iii) with the length of each of the faces having the adhesive being at least approximately the distance between the outer corner portions of the eyes of an average sized adult whereby each of the strips may be applied to the proximal edge end portion of the piece or over existing adhesive such as when the existing adhesive deteriorates.

* * * * *